(12) United States Patent
Fuentes et al.

(10) Patent No.: US 8,765,785 B2
(45) Date of Patent: Jul. 1, 2014

(54) SOLIFENACIN SALTS

(75) Inventors: Gerardo Gutiérrez Fuentes, Boecillo (ES); Antonio Lorente Bonde-Larsen, Boecillo (ES); Jaime del Campo López-Bachiller, Boecillo (ES); Celso Sandoval Rodríguez, Boecillo (ES); Yolanda Fernández Sainz, Boecillo (ES)

(73) Assignee: Crystal Pharma, S.A.U., Boecillo (ES)

( * ) Notice: Subject to any disclaimer, the term of this patent is extended or adjusted under 35 U.S.C. 154(b) by 0 days.

(21) Appl. No.: 13/805,828

(22) PCT Filed: Jul. 5, 2011

(86) PCT No.: PCT/EP2011/061314
§ 371 (c)(1),
(2), (4) Date: Apr. 11, 2013

(87) PCT Pub. No.: WO2012/004264
PCT Pub. Date: Jan. 12, 2012

(65) Prior Publication Data
US 2013/0203804 A1    Aug. 8, 2013

Related U.S. Application Data

(60) Provisional application No. 61/472,807, filed on Apr. 7, 2011.

(30) Foreign Application Priority Data

Jul. 5, 2010    (EP) .................................... 10168415

(51) Int. Cl.
*C07D 453/02* (2006.01)
*A61K 31/439* (2006.01)

(52) U.S. Cl.
CPC ............. *C07D 453/02* (2013.01); *A61K 31/439* (2013.01)

USPC .......................................... 514/305; 546/137

(58) Field of Classification Search
None
See application file for complete search history.

(56) References Cited

U.S. PATENT DOCUMENTS

| | | |
|---|---|---|
| 2008/0039516 A1 | 2/2008 | Sugihara et al. |
| 2008/0103171 A1 | 5/2008 | Umejima et al. |

FOREIGN PATENT DOCUMENTS

| | | |
|---|---|---|
| EP | 0 801 067 B1 | 3/2003 |
| EP | 1 726 304 A1 | 3/2005 |
| EP | 1 714 965 A1 | 10/2006 |
| WO | WO 2008/011462 A2 | 1/2008 |
| WO | WO 2008/077357 A2 | 7/2008 |
| WO | WO 2009/087664 A1 | 7/2009 |
| WO | WO 2009/139002 A2 | 11/2009 |
| WO | WO 2010/012459 A2 | 2/2010 |

OTHER PUBLICATIONS

Berge, Stephen M. et al., "Pharmaceutical Salts" Journal of Pharmaceutical Sciences, Jan. 1977, pp. 1-19, vol. 66, No. 1.
International Search Report for PCT/EP2011/061314, dated Oct. 7, 2011.

*Primary Examiner* — Zinna Northington Davis
(74) *Attorney, Agent, or Firm* — Knobbe Martens Olson & Bear LLP

(57) ABSTRACT

The invention concerns fumarate salts of solifenacin, as well as pharmaceutical compositions comprising fumarate salts of solifenacin. The invention furthermore concerns a process for preparing solifenacin and salts thereof. The fumarate salt provides improved properties over the known solifenacin salts, especially in terms of its stability. The novel process for its preparation is furthermore improved over known processes for preparing solifenacin in that it provides a higher yield and recovers a greater amount of starting material.

17 Claims, 10 Drawing Sheets

Figure 1: PXRD of Crystalline form of solifenacin Fumarate
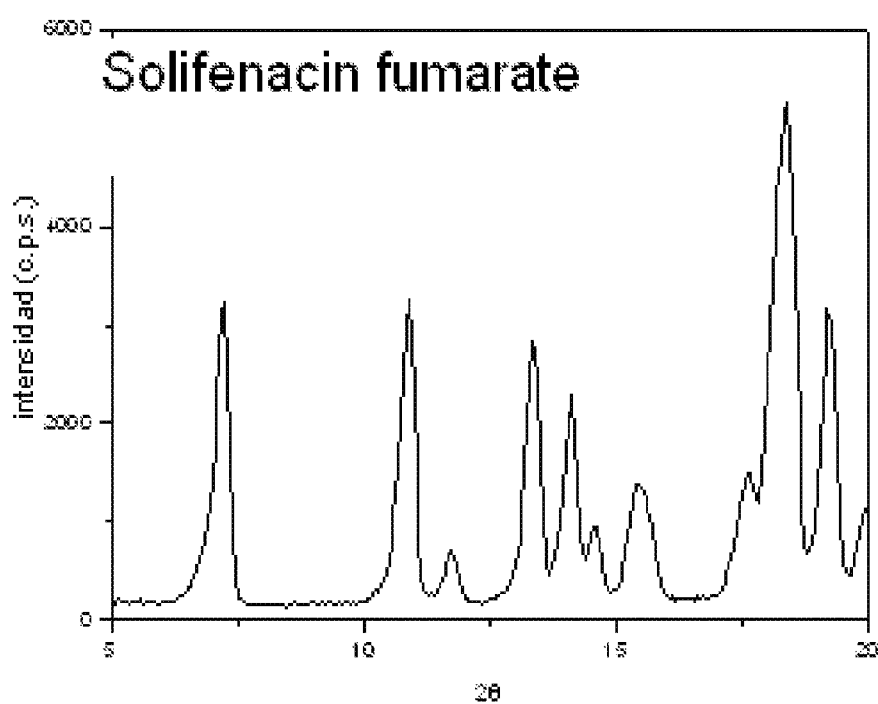

Figure 2: PXRD of Lyophilised solifenacin Fumarate.
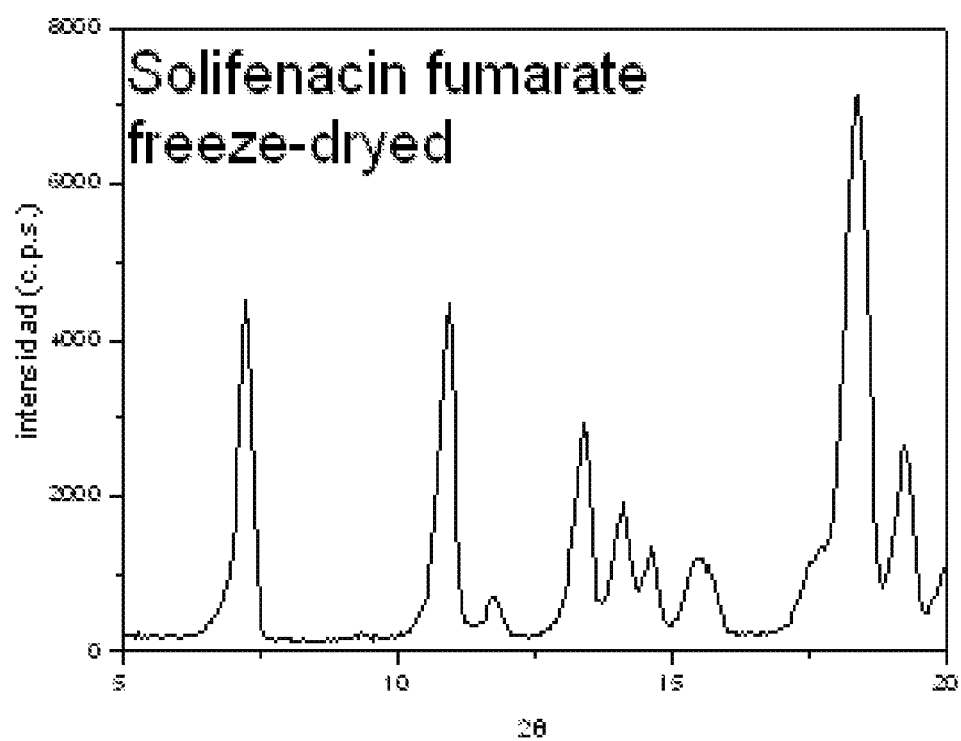

Figure 3: PXRD of Crystalline form of solifenacin Succinate.
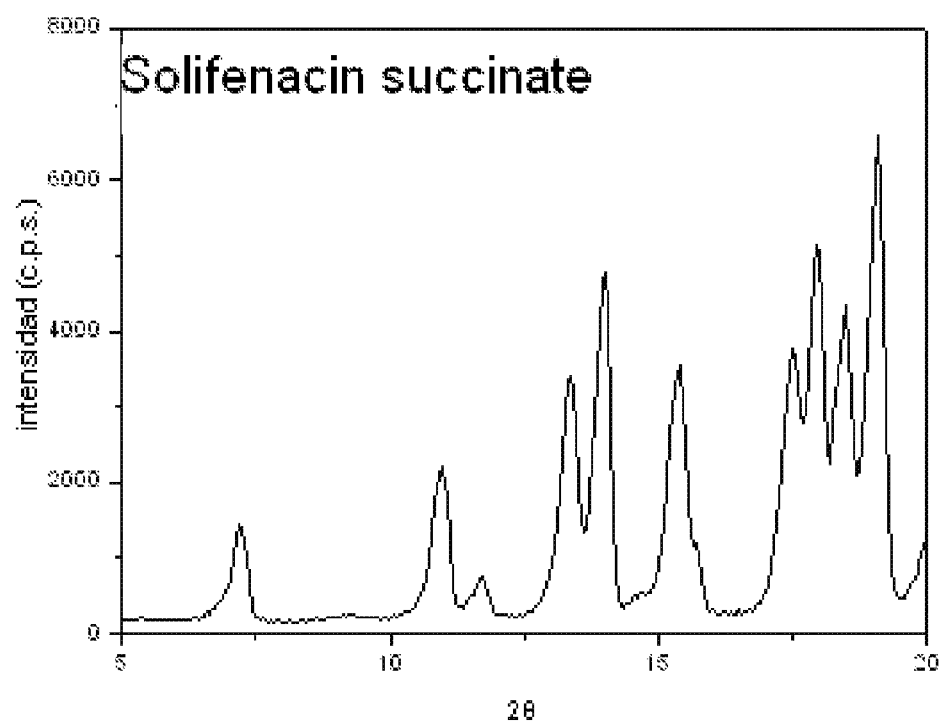

Figure 4: PXRD of Lyophilised of solifenacin Succinate.
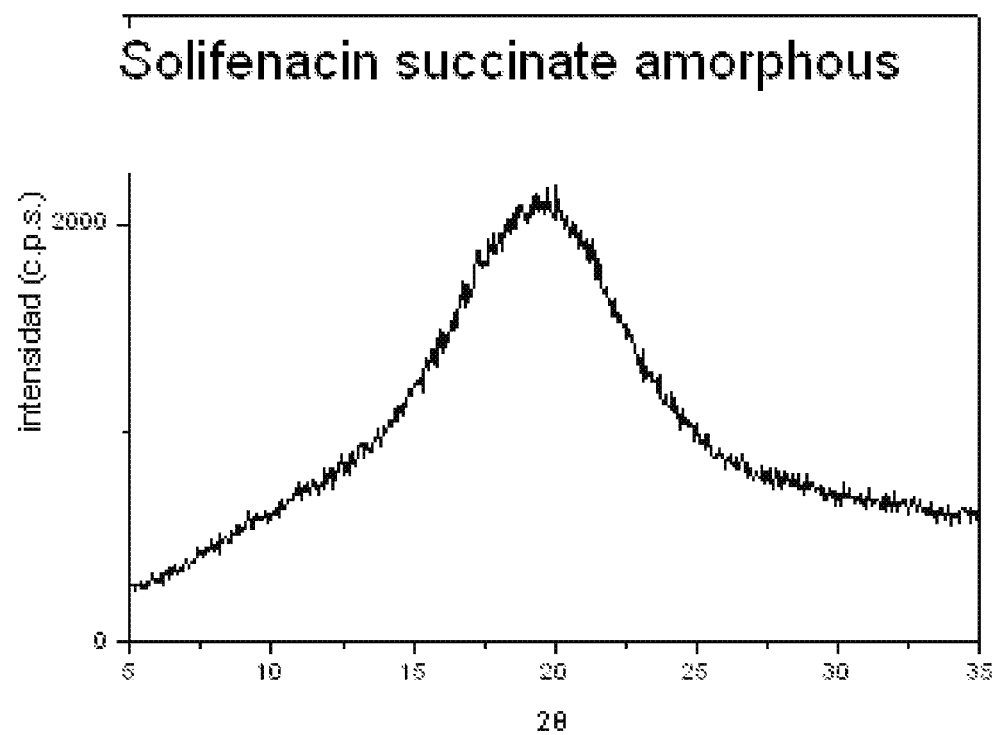

Figure 5: DSC of Crystalline form of solifenacin Fumarate:
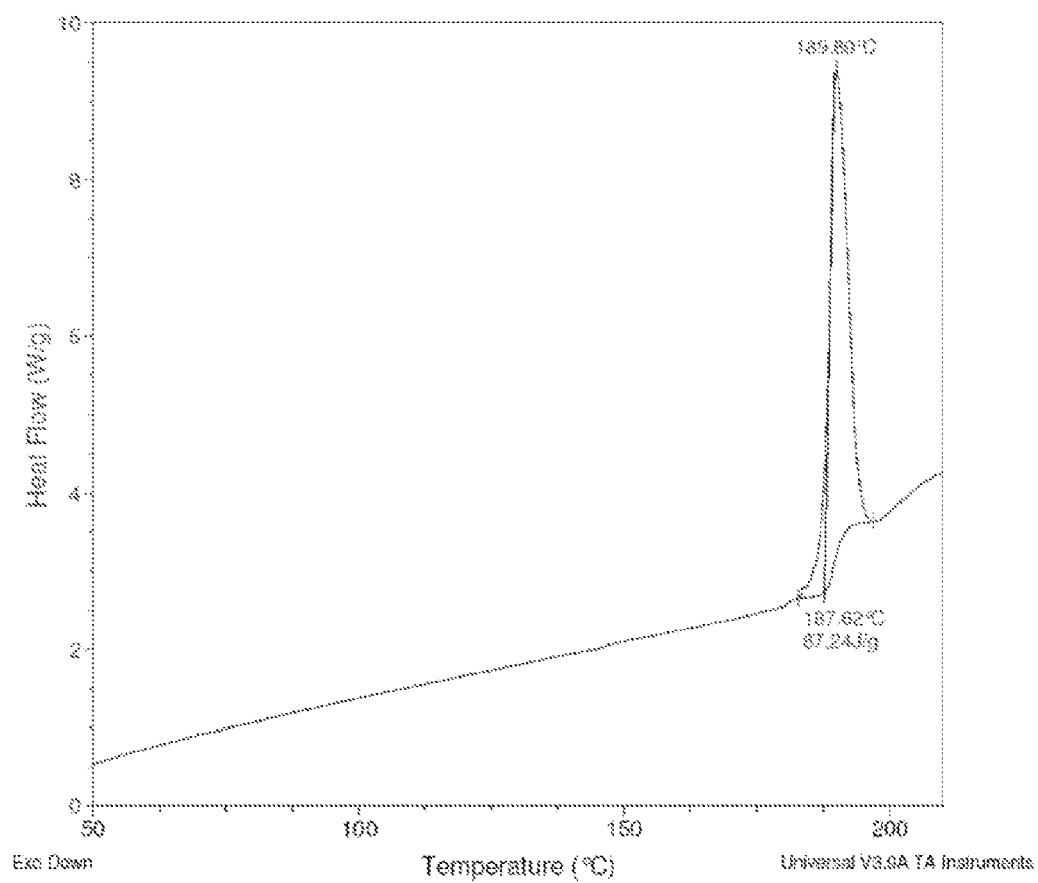

Figure 6: DSC of Lyophilised solifenacin Fumarate.
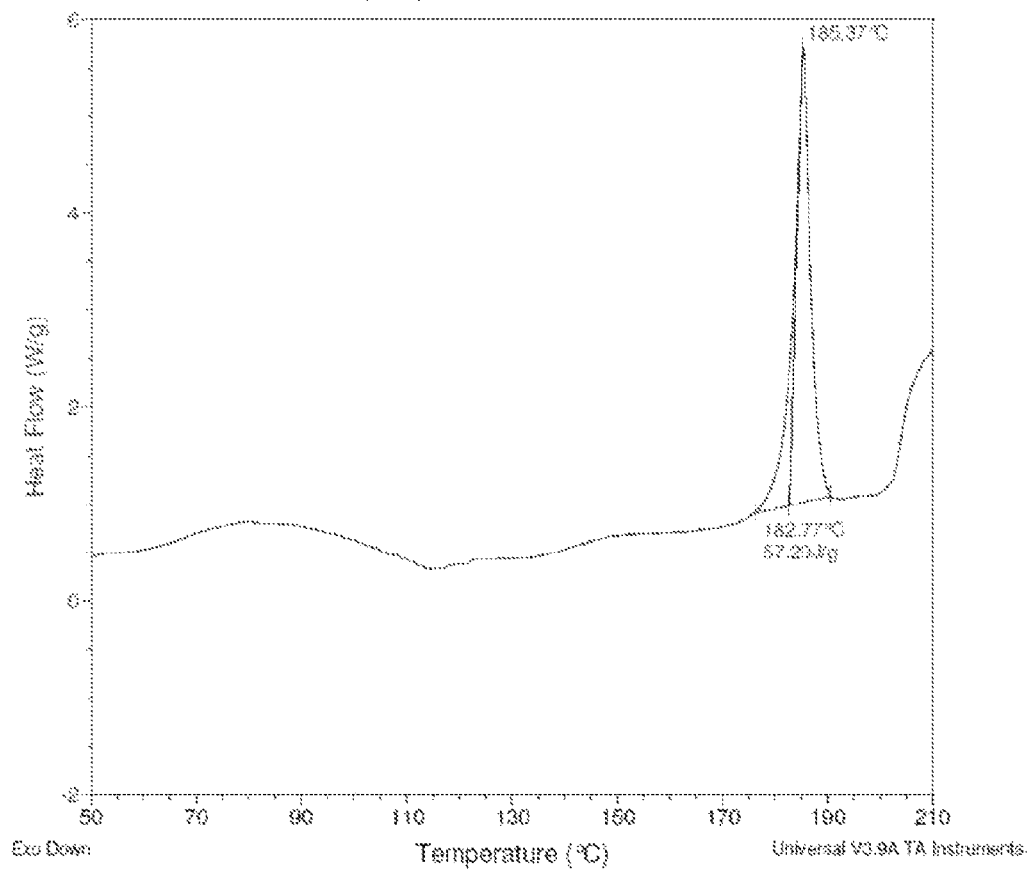

Figure 7: DSC of Crystalline form of solifenacin Succinate
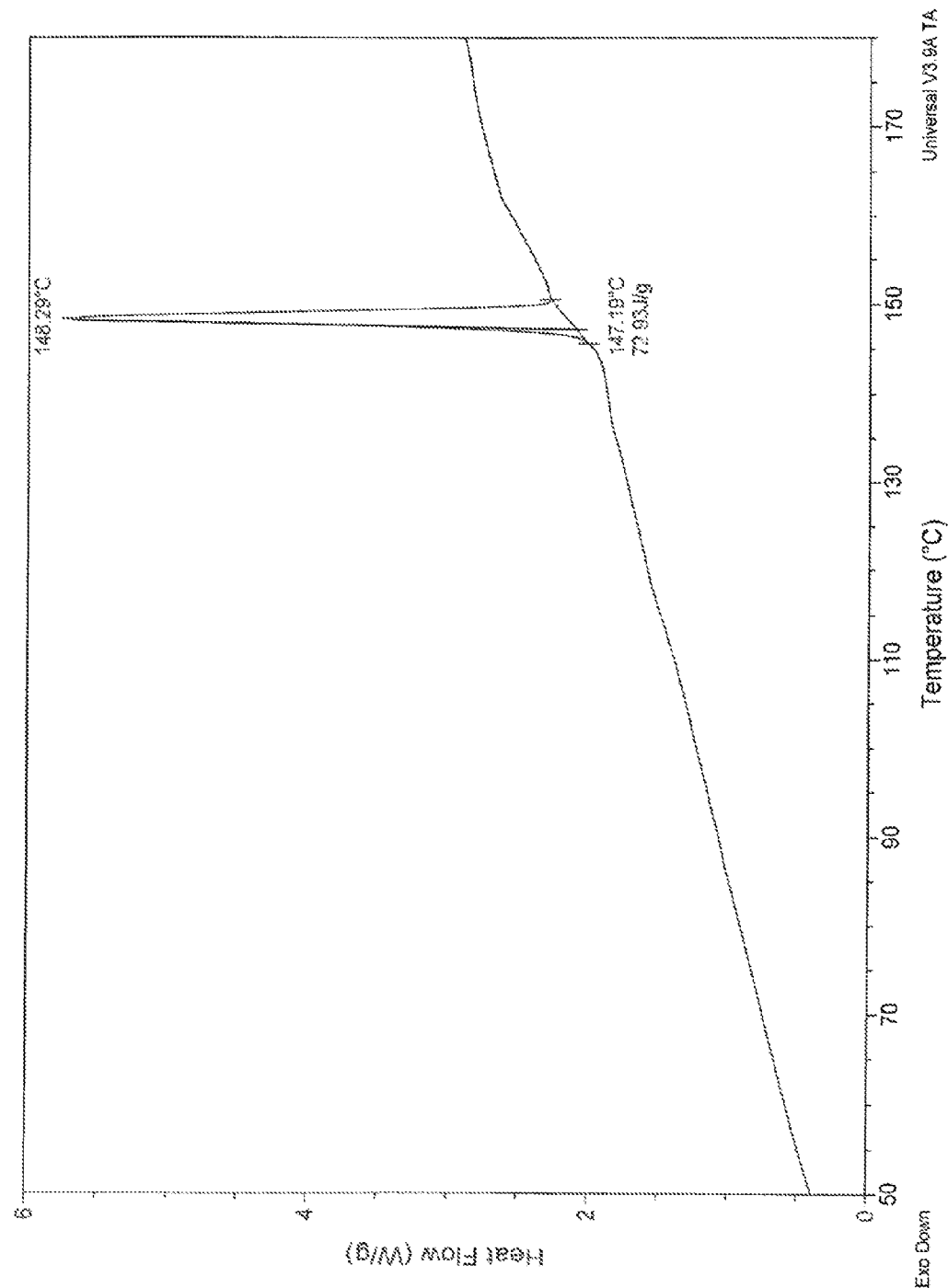

Figure 8: DSC of of Lyophilised solifenacin Succinate
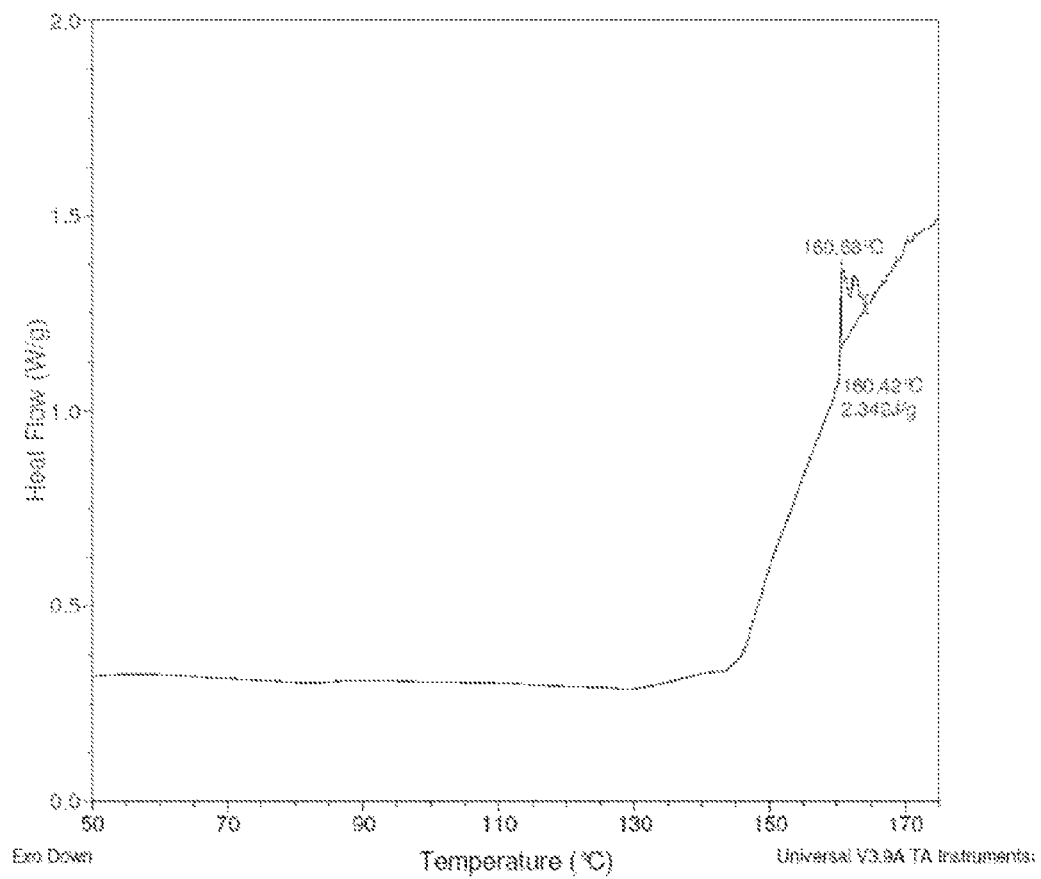

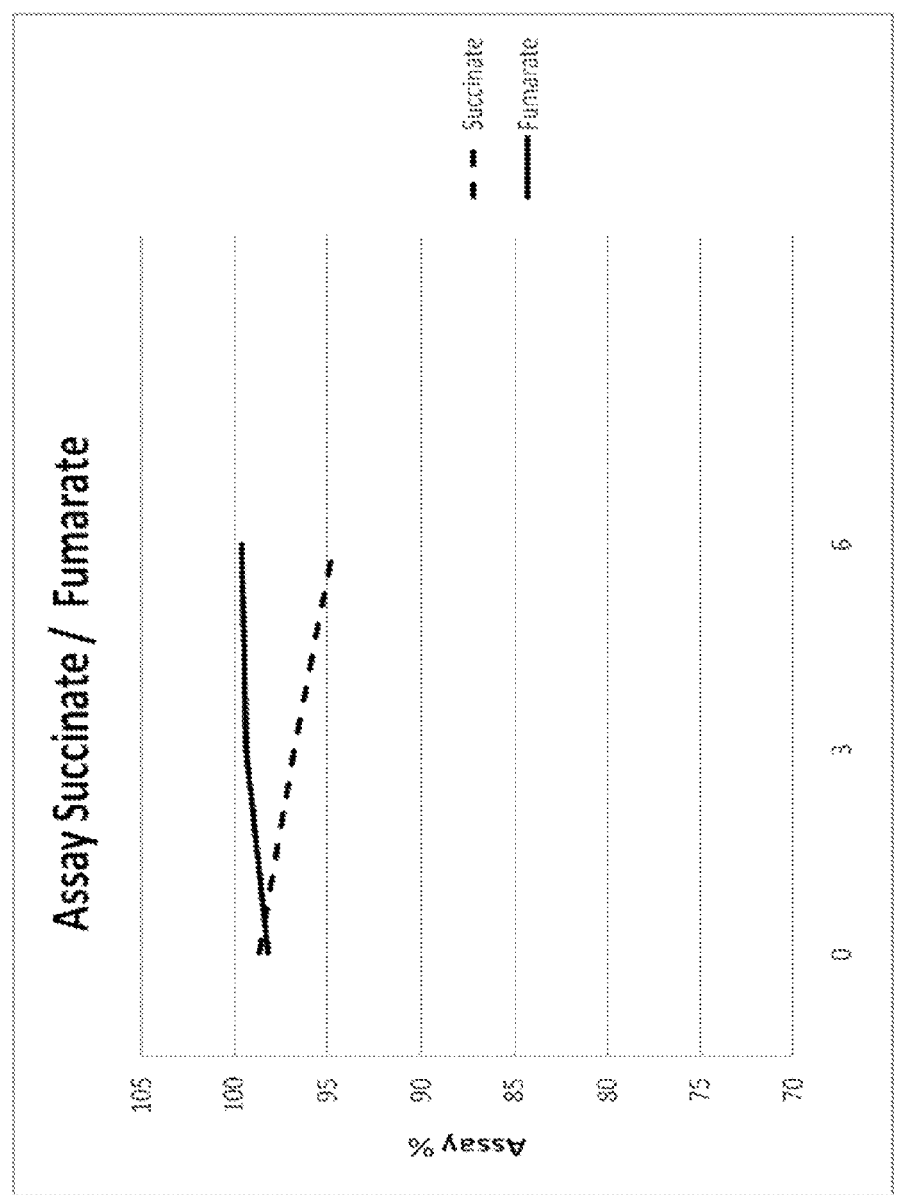
Figure 9: Amounts of solifenacin in solifenacin succinate and fumarate tablets.

Figure 10: Impurity amounts in solifenacin succinate and fumarate tablets.
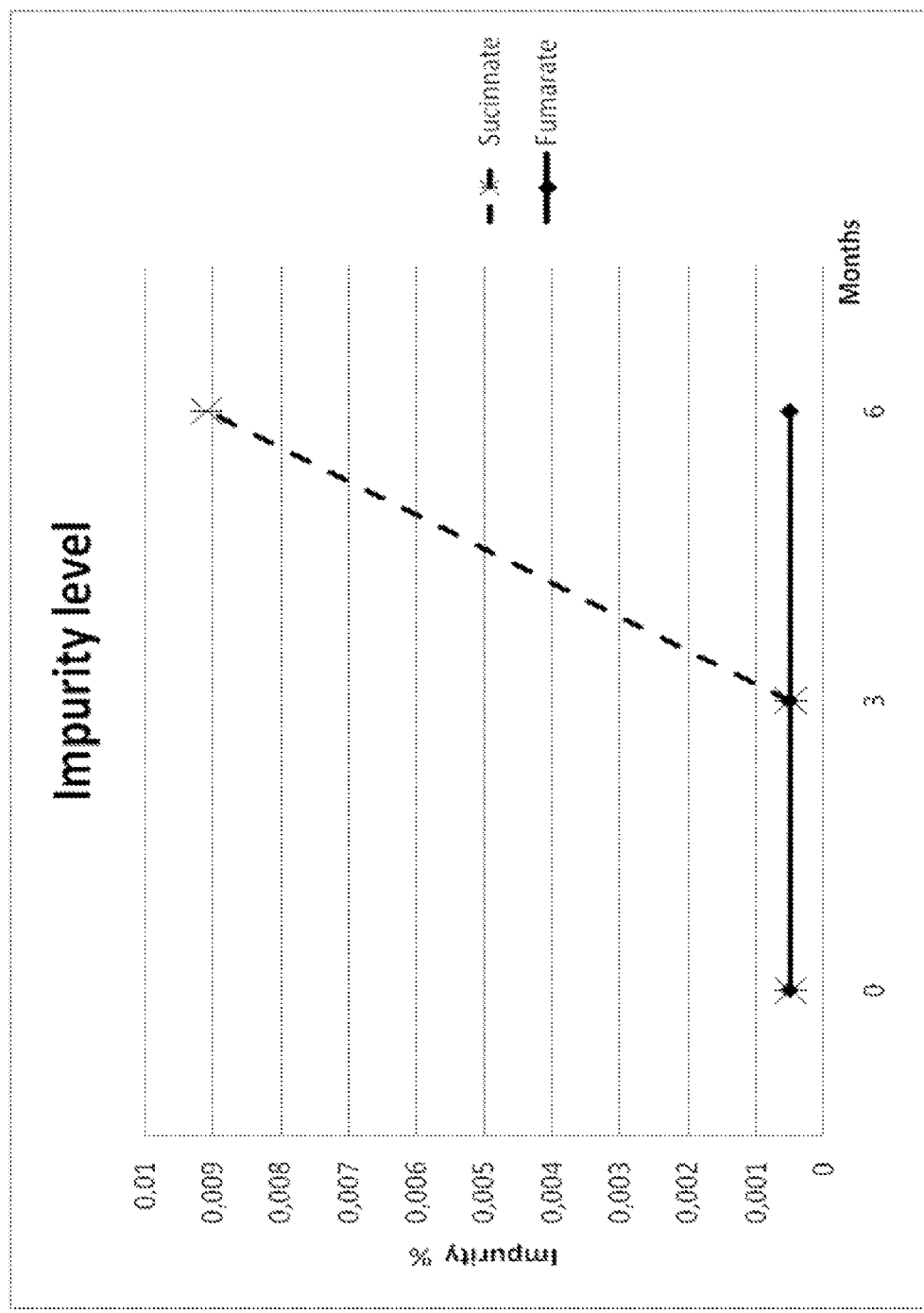

SOLIFENACIN SALTS

CROSS REFERENCE TO RELATED APPLICATIONS

This application is a U.S. National Phase Application of PCT International Application Number PCT/EP2011/061314, filed on Jul. 5, 2011, designating the United States of America and published in the English language, which is an International Application of and claims the benefit of priority to European Patent Application No. 10168415.7, filed on Jul. 5, 2010, and U.S. Provisional Application No. 61/472,807, filed on Apr. 7, 2011. The disclosures of the above-referenced applications are hereby expressly incorporated by reference in their entireties.

FIELD OF THE INVENTION

The present invention concerns fumarate salts of solifenacin, as well pharmaceutical compositions comprising fumarate salts of solifenacin. The invention furthermore concerns a process for preparing solifenacin and salts thereof.

BACKGROUND OF THE INVENTION

Solifenacin (1-azabicyclo[2.2.2]oct-8-yl(1S)-1-phenyl-3,4-dihydro-1H-isoquinoline-2-carboxylate) is known in the art as a urinary antispasmodic useful for treating overactive bladder with or without urge incontinence. Solifenacin was disclosed in EP 0 801 067 together with the oxalate salt thereof.

Solifenacin is presently being sold as solifenacin succinate (Vesicare®) by Astellas Pharma. Solifenacin succinate was first disclosed in EP 1 714 965 A1, wherein it is also disclosed that the succinate salt results in a purer end product. Other salts of solifenacin, such as the tartrate, maleate, and glutarate salts thereof are disclosed in WO 2008/011462, WO 2008/077357, WO 2009/087664, and WO 2010/012459.

Solifenacin succinate does, however, display certain stability problems. In US 2008/039516 and US 2008/0103171 it is disclosed how solifenacin succinate lacks stability when formulated by a wet granulation process. This is, according to US 2008/039516 and US 2008/0103171, due to formation of the amorphous form of solifenacin succinate during the manufacturing process. It was found that a content of the amorphous form of 77% or less was necessary to maintain product stability. Otherwise, the amount of the main degradation product, an oxidized form of solifenacin (labelled "F1" in the two US publications), will increase above the acceptable level of 0.4%.

It was additionally found that using polyethylene glycol (PEG) as a binder for the granulation avoided the stability problems, irrespective of the manufacturing process. Another proposed solution for maintaining the impurity below 0.4% was to adjust the moisture content in the solifenacin succinate during wet granulation.

According to the guidelines of The International Conference on Harmonisation of Technical Requirements for Registration of Pharmaceuticals for Human Use (ICH) section Q3A(R2), Impurities in new drug substances, the qualification threshold for a known impurity must be 0.15% or less.

Moreover, the "Impurity F1" as an oxidized form of Solifenacin may be considered as a potential genotoxic impurity. In such case, the qualification threshold would be much lower than 0.15%.

Therefore, despite the attempts in the art for finding solutions for this stability problem, it is necessary to reduce the amount of "Impurity F1" even further.

For other salts of solifenacin, WO 2010/012459 discloses that grinding of the salts in crystalline form leads to the amorphous form. In other words, the salts disclosed in WO 2010/012459 become amorphous under the conditions used for preparing tablets containing the salts. These salts are therefore likely to experience the same stability problems as the succinate salt.

The state of the art reveals several ways to obtain Solifenacin. Most of them have as a common characteristic the use of 3R-quinuclidinol. Solifenacin was first synthesized in EP 0 801 067 by reacting 1-phenyl-1,2,3,4-tetrahydroisoquinoline with ethyl chloroformate. The resulting carbamate was subsequently reacted with quinuclidinol in the presence of sodium hydride, resulting in solifenacin final compound together with some diastereoisomeric and enantiomeric impurities. The carbamate and the quinuclidinol were reacted at a molar ratio of 1:1. No information is provided concerning the purity of the end product.

In WO 2008/011462 is disclosed a similar synthesis for preparing solifenacin, using the same reactants in toluene as a solvent. It is specified that the amount of 3R-quinuclidinol should be less than 1.5 molar equivalents due to the high cost of this reagent. WO 2009/139002 concerns the recovery of 3R-quinuclidinol from the mother liquors obtained from the preparation of solifenacin. Sodium hydroxide or potassium hydroxide is added to the mother liquor for recovering 3R-quinuclidinol. The molar ratio of 3R-quinuclidinol to carbamate is around 3:1. No information is provided concerning the yield of recovered 3R-quinuclidinol.

The final solifenacin product being prepared for formulation as a medicine must be of the required purity. Therefore, it has been proposed to use various salts of solifenacin for purifying the final product in EP 1 714 965 A1 (succinate salt used for purification), WO 2008/077357 (tartrate salt used for purification), and WO 2009/087664 (hydrochloride and oxalate salts used for purification).

There is, however, still a need for a solifenacin salt of higher stability than the commercially sold succinate salt, as well as pharmaceutical formulations thereof, in order to ensure the shelf-life of the commercial product during distribution and sale. In addition, there is also still a need for a more efficient process for preparing solifenacin and salts thereof with higher yields and a higher purity of the final product. There is a further need for an improved recovery of 3R-quinuclidinol.

SUMMARY OF THE INVENTION

In a first aspect, the present invention concerns a fumarate salt of solifenacin.

In another aspect, the present invention concerns a pharmaceutical composition comprising a fumarate salt of solifenacin as well as one or more pharmaceutically acceptable carriers.

In yet another aspect, the present invention concerns a process for preparing solifenacin or a pharmaceutically acceptable salt thereof comprising the steps of:
a) reacting solifenacin base with fumaric acid to form a fumarate salt thereof; and
b) optionally transforming the fumarate salt obtained in step d) to solifenacin base and/or a different pharmaceutically acceptable salt of solifenacin.

BRIEF DESCRIPTION OF THE FIGURES

FIG. 1 shows a powder X-ray diffractogram (PXRD) of a crystalline form of solifenacin fumarate.

FIG. 2 shows a PXRD of lyophilised solifenacin fumarate.

FIG. 3 shows a PXRD of a crystalline form of solifenacin succinate.

FIG. 4 shows a PXRD of lyophilised of solifenacin succinate.

FIG. 5 shows a differential scanning chromatogram (DSC) of a crystalline form of solifenacin fumarate.

FIG. 6 shows a DSC of lyophilised solifenacin fumarate.

FIG. 7 shows a DSC of a crystalline form of solifenacin succinate.

FIG. 8 shows a DSC of lyophilised solifenacin succinate.

FIG. 9 shows the amount of solifenacin over time in tablets containing solifenacin succinate and solifenacin fumarate, respectively.

FIG. 10 shows the amount of "F1" impurity over time in tablets containing solifenacin succinate and solifenacin fumarate, respectively.

DETAILED DESCRIPTION OF THE INVENTION

In a first aspect, the present invention concerns a fumarate salt of solifenacin. Fumaric acid contains two acidic hydrogen atoms, whereas each solifenacin molecule normally only accepts one hydrogen atom in acid-base reactions. A fumarate salt of solifenacin may therefore contain solifenacin and fumaric in the molar ratio 1:2 or 1:1.

In a presently preferred embodiment, the fumarate salt of the invention is the hydrogenfumarate salt of solifenacin, i.e. solifenacin and fumaric acid in the molar ratio 1:1.

Vesicare is presently approved for sale as tablets and contains the succinate salt of solifenacin in solid form. The solid form of the fumarate salt of the present invention may in principle be provided both as an amorphous salt or as a crystalline salt. In one embodiment, said solid form of the fumarate salt of the invention is substantially only crystalline. By "substantially only crystalline" is meant that the amorphous form is not detectable by any of the presently available analytical methods, such as Differential scanning calorimetry (DSC), X-ray powder diffraction, NMR, IR, solid state NMR, and Differential thermal analysis.

Pharmaceutical Compositions

In another aspect, the solifenacin fumarate salt of the invention is preferably administered in a composition including a pharmaceutically acceptable carrier or excipient. The term "pharmaceutically acceptable" means a carrier or excipient that does not cause any untoward effects in patients to whom it is administered. Such pharmaceutically acceptable carriers and excipients are well known in the art (Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

The exact dose to be administered depends on the circumstances. Normally, the dose should be capable of preventing or lessening the severity or spread of the condition or indication being treated. It will be apparent to those of skill in the art that an effective amount of the solifenacin fumarate salt of the invention depends, inter alia, upon the disease, the dose, the administration schedule, whether the solifenacin salt of the invention is administered alone or in conjunction with other therapeutic agents, the general health of the patient, and the like.

The pharmaceutical composition may be formulated in a variety of forms, including liquid, gel, lyophilised, powder, compressed solid, or any other suitable form. The preferred form will depend upon the particular indication being treated and will be apparent to one of skill in the art.

The pharmaceutical composition may be administered orally, subcutaneously, intravenously, intracerebrally, intranasally, transdermally, intraperitoneally, intramuscularly, intrapulmonary, vaginally, rectally, intraocularly, or in any other acceptable manner, e.g. using PowderJect or ProLease technology. The composition can be administered continuously by infusion, although bolus injection is acceptable, using techniques well known in the art, such as pumps or implantation. In some instances the composition may be directly applied as a solution or spray. The preferred mode of administration will depend upon the particular indication being treated and will be apparent to one of skill in the art. However, the currently preferred mode of administration is via the oral route.

The pharmaceutical composition of the invention may be administered in conjunction with other therapeutic agents. These agents may be incorporated as part of the same pharmaceutical composition or may be administered separately from the composition of the invention, either concurrently or in accordance with any other acceptable treatment schedule.

Oral Administration

For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include a tablet, capsule, gelcap, powder, granule, sachet or a pill. In one embodiment of the invention, the pharmaceutical composition of the invention is a tablet. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The solifenacin salt of the invention may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the solifenacin salt of the invention may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. In a presently preferred embodiment, the pharmaceutical composition of the invention is substantially free from polyethylene glycol. In this context, "substantially free from polyethylene glycol" means that the pharmaceutical composition does not contain polyethylene glycol in an amount detectable with currently available analytical methods.

The pharmaceutical compositions may be subjected to conventional pharmaceutical operations such as sterilisation and/or may contain conventional adjuvants such as preservatives, stabilisers, wetting agents, emulsifiers, buffers, fillers, etc.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, sweeteners, flavoring agents and perfuming agents.

Medical Use

The compound and composition according to the present invention are, as is the case for the succinate salt, useful as a medicine in the treatment of overactive bladder. Hence, one aspect of the invention is the compound or composition of the present invention for use in medicine. Another aspect of the invention is the compound or composition of the present for use in the treatment of overactive bladder.

Process for the Preparation of Solifenacin and Salts Thereof.

Yet another aspect of the invention concerns a process for preparing solifenacin or a pharmaceutically acceptable salt thereof comprising the steps of:
a) reacting solifenacin base with fumaric acid to form a fumarate salt thereof; and
b) optionally transforming the fumarate salt obtained in step d) to solifenacin base and/or a different pharmaceutically acceptable salt of solifenacin.

In one embodiment, steps a) and b) are preceded by the following steps:
a') reacting 1(S)-1-phenyl-1,2,3,4-tetrahydroisoquinoline with a $C_{1-6}$ alkyl chloroformate, such as ethyl chloroformate, to form the corresponding carbamate;
b') reacting the carbamate resulting from step a) with 3R-quinuclidinol in the presence of a strong base, such as sodium or potassium ethoxide, sodium or potassium methoxide, sodium or potassium isopropoxide, sodium or lithium amide, or sodium hydride, preferably sodium hydride, to form solifenacin base;
c') optionally isolating solifenacin base;
wherein the solifenacin base used in step a) is the base obtained in step b') or step c').

In one embodiment, the molar ratio of 3R-quinuclidinol to carbamate in step b') is at least 2.1:1, such as at least 2.2:1, 2.3:1, 2.4:1, 2.5:1, 2.6:1, 2.7:1, 2.8:1, 2.9:1, or 3:1.

The term "strong base" as used in connection with the process according to the invention means a base sufficiently strong to drive the reaction between 3R-quinuclidinol and carbamate in step b'). The skilled person will easily establish which bases commonly applied in organic reactions are sufficiently strong to drive the reaction between 3R-quinuclidinol and carbamate in step b'). Examples of these bases are sodium and potassium ethoxide, sodium and potassium methoxide, sodium and potassium isopropoxide, sodium and lithium amide, and sodium hydride. In a presently preferred embodiment, the strong base used in the process according to the invention is sodium hydride.

In the present context, the term "$C_{1-6}$ alkyl" is intended to mean a linear or branched saturated hydrocarbon group having from one to six carbon atoms, such as methyl, ethyl, n-propyl, isopropyl, n-butyl, isobutyl, sec-butyl, tert-butyl, n-pentyl, isopentyl, neopentyl and n-hexyl. In a presently preferred embodiment of the process according to the invention, the $C_{1-6}$ alkyl chloroformate is ethyl chloroformate.

The inventors of the present invention have found that using an excess of 3R-quinuclidinol provides a better yield than in the processes known in the art. In addition, the excess of 3R-quinuclidinol may be recovered from the solvent after formation of solifenacin base.

In one embodiment, the solvent in step b') is a mixture of a non-polar solvent, such as toluene, and a polar solvent, such as dimethylformamide. The skilled person will know that the polar solvent for the reaction in step b) should not contain any functional groups competing with the hydroxyl group in 3R-quinuclidinol for reacting with the strong base. As an example, ethanol and other alcohols are not suitable polar solvents for use in step b').

The term "non-polar solvent" as used herein means a carbon-containing solvent generally having a dielectric constant of less than 5. Non-limiting examples of non-polar solvents are hexane, benzene, toluene, diethyl ether, and chloroform. In certain embodiments, the term "non-polar solvent" as used herein means a carbon-containing solvent generally having a dielectric constant of less than 5, wherein said solvent is at the same time aprotic.

The non-polar solvent may be made up of two or more non-polar solvents, i.e. being a mixture of such solvents.

In one embodiment, the non-polar solvent is toluene. In another embodiment the non-polar solvent is selected from the group consisting of benzene, hexane, and xylene.

In one embodiment of the invention, the non-polar solvent is both non-polar and aprotic, e.g. the non-polar solvent has a dielectric constant of less than 5 and a $pK_a$ of 5 or more, such as a dielectric constant of less than 5 and a $pK_a$ of 6 or more, such as a dielectric constant of less than 5 and a $pK_a$ of 7 or more, such as a dielectric constant of less than 5 and a $pK_a$ of 8 or more, such as a dielectric constant of less than 5 and a $pK_a$ of 10 or more. Examples of non-polar, aprotic solvents in accordance with the invention are hexane, benzene, toluene, diethyl ether, and chloroform.

In still another embodiment the non-polar aprotic solvent is selected from the group consisting of 2-methylbutane, n-hexane, 2,3-dimethylbutane, n-heptane, 2-methylhexane, 2,2,3-trimethylbutane, n-octane, 2,4-dimethylhexane, 2,2,4-trimethylpentane, 2-methyloctane, 3-methyloctane, 2,6-dimethylheptane, 2,7-dimethyloctane, n-hexadecane, 7,8-dimethyltetradecane, cyclopentane, methylcyclopentane, ethylcyclopentane, isopropylcyclopentane, n-butylcyclopentane, n-hexylcyclopentane, 2-cyclopenyloctane, 1,4-dicyclopentylbutane, cyclohexane, decalin, benzene, toluene, ethylbenzene, o-xylene, m-xylene, p-xylene, isopropylbenzene, 1,3,5-trimethylbenzene, n-butylbenzene, sec-butylbenzene, tert-butylbenzene, 1-methyl-4-isopropylbenzene, dimethylbenzene, 1,3,5-trimethyl-2-ethylbenzene, 1,3,5-trimethyl-2-propylbenzene, 1,3,5-trimethyl-2-allylbenzene, 2-phenyl-2,4,6-trimethylheptane, 1-methyl-2-phenylcyclopentane, 1-ethyl-2-phenylcyclopentane, naphtalene, alfa-methylnaphtalene, 2-methylbut-2-ene, hexene-1,2,3-dimethylbut-1-ene, heptene-1, diisobutylene. The aprotic non-polar solvent may also be made up of two or more aprotic non-polar solvents, i.e. being a mixture of such solvents.

In another embodiment, the aprotic non-polar solvents are selected from the group of solvents of similar structure as toluene, such as, benzene, xylene, ethylbenzene, trimethylbenzenes, ethyltoluenes, propylbenzenes, tetramethylbenzenes, ethyldimethylbenzenes, diethylbenzenes, methylpropylbenzenes, ethylpropylbenzenes, triethylbenzenes, diisopropylbenzenes, and mixtures thereof.

The term "polar solvent" as used herein means a carbon-containing solvent generally having a dielectric constant of more than 10, such as more than 15, such as more than 20, such as more than 25, or more than 30. Non-limiting examples of polar solvents are dimethylformamide (DMF), ethyl acetate, dimethyl sulfoxide (DMSO), dioxane, and acetonitrile. In certain embodiments, the term "polar solvent" as used herein means a carbon-containing solvent generally having a dielectric constant of more than 10, such as more than 15, such as more than 20, such as more than 25, or more than 30, wherein said solvent is at the same time aprotic.

In a further embodiment of the process according to the invention, the polar solvent is present in an amount of 1 to 20% (v/v) of the combined solvent volume, such as in an amount of 3 to 15% (v/v), or 5 to 10% (v/v).

Recovery of 3R-Quinuclidinol

As mentioned above, the excess 3R-quinuclidinol used in the process for producing solifenacin and salts thereof may be recovered. In one embodiment, the excess 3R-quinuclidinol resulting from step b') of the process according to the invention is recovered by cooling the mixture from said step b') to a temperature not exceeding 15° C., such as not exceeding 10° C., preferably not exceeding 5° C., stirring the mixture for at least 20 minutes, such as at least 30 minutes, at said temperature, and collecting the formed precipitate, e.g. with a filter.

In another embodiment for recovering excess 3R-quinuclidinol water is added upon cooling of the mixture from said step b') in an amount of up to 20% (v/v) of the non-polar solvent, such as in an amount of 0.3 to 10% (v/v), such as in an amount of 0.5 to 5% (v/v), such as in an amount of 0.7 to 3% (v/v), preferably in an amount 1.0 to 2.0% (v/v).

Purification of the End Product

The inventors of the present invention have found that the product according to the process of the present invention may be further purified by first converting it to a fumarate salt of solifenacin. This applies both for solifenacin base as well as salts thereof, including the fumarate salt as the final product.

Accordingly, in a further embodiment of the present invention the fumarate salt is obtained quantitatively by reacting solifenacin base with fumaric acid in a suitable solvent, such as for example (but not limited to) acetone, ethyl acetate, toluene, ethanol, water or a mixture of these solvents. The formed fumarate salt may optionally be converted back to solifenacin base and/or further solifenacin salts, such as a succinate salt.

In a particular embodiment, solifenacin base resulting from the reaction mixture in step b) of the process of the invention or as isolated from step c) of the process of the invention and redissolved for example in toluene or ethyl acetate, can be added to a solution in acetone or acetone/water of fumaric acid to form a precipitate of the salt. Said salt can be isolated by filtration or optionally, in a quantitative manner, by means of partial distillation of the solvents and isolation, preferably by filtration.

The inventors have also found that the fumarate salt obtained may be further purified. Accordingly, in another embodiment of the process according to the invention, a fumarate salt of solifenacin is further purified by suspending said fumarate salt in a mixture of polar solvents, such as ethyl acetate and ethanol, and stirring for a time period sufficient to obtain (S,R)-solifenacin fumarate with an optical purity so that the amount of each of the (R,R) and (S,S)-diastereoisomers and (R,S) enantiomer, is 0.2% or less of the total amount of solifenacin fumarate.

Solifenacin fumarate of high purity, with all impurities in an amount of 0.2% or less can be obtained from solifenacin base in two steps: a) a salt formation step wherein the fumarate salt is isolated quantitatively and b) a simple resuspension step wherein the fumarate salt is isolated in pure form. The overall yield of purified solifenacin fumarate is 85% from Tetrahydroisoquinoline as starting material in the process according to the invention.

If necessary, solifenacine fumarate with all the impurities in an amount of less than 0.1%, such as below detection level, may be obtained by another resuspension step using the same solvents.

In comparison, in the process disclosed in the application EP 1 714 965, which concerns the purification of solifenacin by means of the formation of the succinate salt in a recrystallization step, the yield obtained is only 60%:

|  | EP 1 714 965 Reference Example 1 → Example 2 Solifenacin base → Solifenacin Succinate | Process according to the invention Scale Batch. Solifenacin base → Solifenacin Fumarate |
| --- | --- | --- |
| (R-R') | 4.51% → 0.05% | 4.07% → 0.18% |
| (S-S') | 2.33% → 0.17% | 1.20% → 0.03% |
| (R-S') | 0.14% → ND | ND → ND |
| Molar yield from Tetrahydroisoquinoline | 60% | 85% |

Additionally, in order to improve the quality/purity of solifenacin succinate obtained according to the patent application EP 1 714 965, it would be necessary to perform another recrystallization step instead of a simple resuspension step as disclosed herein with the fumarate salt.

Furthermore, the purification by the use of the tartrate salt described in the patent application WO2008/077357, requires the use of three recrystallization steps with an overall yield of only 66% in order to have all impurities in an amount of 0.2% or less (see example 9 of WO2008/077357).

Other attempts realized using for example the Chlorohydrate or oxalate salts (according to EP 1 714 965) failed in obtaining the desired purity necessary for pharmaceutical use.

Stability of Solifenacin Fumarate

As mentioned above, a problem in the art regarding the stability of solifenacin succinate consists in the conversion of the crystalline form of solifenacin succinate to the amorphous form during wet granulation. The amorphous form of solifenacin succinate does not meet the desired stability criteria.

Solifenacin fumarate is considered to have improved stability over solifenacin succinate. Without being bound by a particular theory, it has been found that one possible reason for the improved stability is that the crystalline form of solifenacin fumarate does not convert to the amorphous form as easily as solifenacin succinate.

One of the best known methods in the art for obtaining amorphous forms of solids, such as salts, is by lyophilization of an aqueous solution of the solid form, such as a salt. In the case of solifenacin succinate, it is quite easy to obtain the desired amorphous form by lyophilization, as it can be seen in its powder X-ray diffractogram (FIGS. 3 and 4 of the crystalline and the amorphous form, respectively) or by Differential Scan calorimetry (DSC) (FIGS. 7 and 8 of the crystalline and the amorphous form, respectively).

However, the lyophilized fumarate salt remains crystalline, as it can also be seen in its powder X-ray diffractogram (FIGS. 1 and 2 of the salt before and after the lyophilization step, respectively) or by DSC (FIGS. 5 and 6 of the salt before and after the lyophilization step, respectively).

In addition, an attempt to make the amorphous form of solifenacin fumarate by abrupt precipitation (as described in Example 6) also failed.

It is known from the prior art that the amorphous form of solifenacin succinate is the source of instability in formulations of solifenacin succinate. Therefore, the lack of conversion of crystalline solifenacin fumarate to the amorphous form under conditions identical to the lyophilization conditions, wherein crystalline solifenacin succinate converts to the amorphous form, make the inventors of the present invention consider the fumarate salt as having improved stability over the succinate salt.

Furthermore, it was found that the instability of the amorphous form of solifenacin succinate could be demonstrated very clearly since it turned colored (from white) in a matter of 2-3 days and the instability of this amorphous form was checked by UV-HPLC (method 2).

In fact, a sample of the colored amorphous form of solifenacin succinate collected after being left to stand for ten days, analyzed by HPLC following the method 2 (described in the examples), showed a new impurity with a relative retention time of 0.93 in an amount of 0.14%.

The crystalline forms of solifenacin succinate and solifenacin fumarate do not have this problem.

In addition, solifenacin fumarate shows a lower solubility in water (11.25 mg/ml) compared to solifenacin succinate (727 mg/ml). Therefore, when the procedure to obtain tablets comprising solifenacin fumarate is carried out by wet granulation, the presence of water is not such an important factor.

Since solifenacin succinate is very soluble in water, the conditions of wet granulation and high pressure favour the dissolution and subsequent conversion into the amorphous form. However, the low solubility of the solifenacin fumarate avoids this problem. The difference in solubility also makes it easier to obtain solid pharmaceutical compositions of solifenacin fumarate since the drying phase is reduced.

To test the stability of solifenacin fumarate, tablets are prepared by wet granulation following the procedure disclosed in US 2008/039516, the contents of which are incorporated in their entirety. A specific example of preparing a tablet containing solifenacin fumarate is given in Example 2 below. The undesired impurities resulting from the tablets (as identified in US 2008/039516) as well as the amorphous form solifenacin fumarate are measured according to the methods disclosed in US 2008/039516.

EXAMPLES

In order to follow the reactions and also to measure and identify the purity of the intermediates, the final products and the impurities, we used the following chromatographic conditions:
HPLC Method 1: To Measure the Diasteroisomeric and Enantiomeric Impurities Associated with Solifenacin.
Column: Chiralpak IA-3, 150 mm×4.6 mm 3 μm
Injection volume: 10 μl
Detector: UV 220 nm
Flow. 1.0 ml/min
Run time: 15 minutes
Temperature: 27° C.
Mobile phase: isopropyl alcohol (IPA) 15/Solution A 85
Solution A: Hexane 900/Ethanol 100/Ethylendiamine 1
HPLC Method 2: To Follow the End Points of the Reactions Performed and the Rest of the Impurities:
Column: C18, 150×4.6 mm, 5 μm
Flow: 1.0 mL/min.
Detection, λ: 210 nm
Temperature: 30° C.
Injection Volume: 10 μL
Mobile phase: Gradient solution A/ACN
Solution A: Weigh about 1.2 g of 1-Octansulphonate Sodium salt HPLC grade and dissolve in a liter of water.

Gradient:

| Time (min) | Dis A % | ACN % |
|---|---|---|
| 0 | 70 | 30 |
| 2 | 70 | 30 |
| 8 | 30 | 70 |
| 13 | 30 | 70 |
| 13.1 | 70 | 30 |
| 18 | 70 | 30 |

Example 1

Synthesis of Solifenacin Fumarate

Formation of Solifenacin Base
1(S)-1,2,3,4-tetrahydroisoquinoline (30 g, 0.143 mol) is dissolved in Toluene (300 mL), then a solution of potassium carbonate (23.7 g, 0.171 mol) in water (60 mL) is charged. The mixture is then cooled to 0° C. and ethylchloroformate (16 ml, 0.168 mol) is slowly added. Once all reagent is charged, the temperature is adjusted to 22° C. and the stirring continues for 40 minutes or until the reaction is finished.

Then, the organic solution is extracted twice with water and once with a 10% solution of sodium chloride. Finally the organic phase is separated and distilled under vacuum until reaching a final volume of 180 mL. Toluene (90 mL) is added to give a solution labeled "Carbamate, solution in toluene".

Toluene (210 mL, KF<0.05%), dimethylformamide (45 mL, KF<0.1%) and 3(R)-Quinuclidinol (55.8 g, 0.439 mol) are charged in the presence of nitrogen. The mixture is cooled to 5° C. and 60% Sodium hydride (33 g, 0.082 mol) is added in the presence of nitrogen. The mixture is stirred at 22° C. for 60 minutes until no more hydrogen is evolved. Then the mixture is heated to 70° C. and the "Carbamate, solution in toluene" is added. The mixture is set to reflux temperature and stirred for 8 hours while distilling off solvent to remove ethanol at intervals with addition of fresh quantity of dry solvent. The reflux/distillation cycle is continued until the reaction is finished.
Recovery of 3R-Quinuclidinol
After the process has been stopped, the solution is cooled to 0/5° C. and water (3 mL) is added over a nitrogen flow, ensuring that the temperature does not rise above 10° C. The mixture is stirred at a temperature of 5/10° C. for 30 minutes and then further cooled to 0/5° C. and filtered. The solid of the filter is labeled as "3R-Quinuclidinol recovered" (32.4 g), whilst the filtration liquids contain the solifenacin base. The yield of recovered 3R-quinuclidinol is about 85% of the 3R-quinuclidinol remaining after completion of the reaction with 1(S)-1-phenyl-1,2,3,4-tetrahydroisoquinoline.
Workup of Solifenacin Base
Over the filtration liquids is added water (60 mL) and the combination is transferred into a separating funnel. The aqueous phase is separated and water (150 mL) is added to the organic phase and the mixture is stirred for 20 minutes. The resulting phases are again allowed to separate. The aqueous phase is separated and water (150 mL) is added to the organic phase. The mixtures is stirred for 20 minutes and the aqueous phase is once again discharged. The organic phase obtained is now collected and labeled as "Solution of Solifenacin base in toluene".
Formation of Solifenacin Fumarate
Acetone (390 mL), water (20 mL) and Fumaric acid (18.3 g, 0.157 mol) are combined in a flask. The mixture is set to reflux until total dissolution of the solid. The "Solution of Solifenacin base in toluene" is then added, whilst maintaining reflux. The mixture is maintained at reflux for 15 minutes and then distilled until reaching a final volume of about 270 ml.

Once this volume is reached, it is cooled slowly until a final temperature of 12° C. Once the temperature is reached, the suspension is filtered. The filtered solid is washed with Ethyl acetate (30 mL) and dried in the vacuum oven at 60° C. to give a white solid ("Solifenacin fumarate crude") in a yield of 93% based on the 1(S)-1,2,3,4-tetrahydroisoquinoline starting material (HPLC-UV, method 1, RR (2.71%), SS (0.71%) and RS (ND)).

Purification of Solifenacin Fumarate

"Solifenacin fumarate crude" (63 g), Ethyl acetate (1008 ml) and Ethanol (95 ml) are combined. The temperature is adjusted to 22° C. and the mixture is stirred under these conditions for 2 hours. After this time, the suspension is filtered and washed with Ethyl acetate (60 ml) to give a white solid in a yield of 92% (HPLC-UV, method 1, RR (0.18%), SS (0.03%) and RS (ND)).

NMR Data:

$^1$H NMR (400 MHz, DMSO): δ 1.50-2.1 (2H, $H_5$, 2H, $H_8$,; 2.17 (1H, $H_4$,); 2.7-3.5 (2H, $H_4$, 2H, $H_7$, 2H, $H_6$, 2H, $H_2$, 1H, $H_3$); 3.84 (1H, $H_3$); 4.88 (1H, $H_3$,); 6.28 (1H, $H_1$); 6.51 (2H, HOOC—C$\underline{H}$=C$\underline{H}$—COOH); 7.20-7.31 (9H, $H_{Ar}$); 13.09 (2H, $\underline{H}$OOC—CH=CH—COO$\underline{H}$) ppm.

$^{13}$C NMR (100 MHz; DMSO): δ 17.37 ($CH_2$, C5'); 20.81 ($CH_2$, C8'); 24.26 (CH, C4'); 27.68 ($CH_2$, $C_4$); 38.88 ($CH_2$, $C_3$); 44.29 ($CH_2$, $C_7$); 45.11 ($CH_2$, $C_6$); 52.77 ($CH_2$, $C_2$); 57.20 (CH, $C_1$); 68.89 (CH, $C_3$); 128.36-128.62 (9CH, $C_{Ar}$); 134.96 (2CH, HOOC—$\underline{C}$H=$\underline{C}$H—COOH); 135.33 (C, $C_5$); 142.05 (C, $C_6$); 145.29 (C, $C_{Ar}$); 155.65 (C, $C_7$), 168.05 (2C, HOO$\underline{C}$—CH=CH—$\underline{C}$OOH); ppm.

MS: (+MS) (m/z): 363.4 ($M^+1$).

Optical Rotation:

$\alpha_D$, [c=1, DMSO]=60.7°, wavelength=589 nm, T=20° C.

Example 2

Synthesis of Solifenacin Succinate

Solifenacin fumarate (52 g) from example 1, Ethyl acetate (260 ml) and potassium carbonate (104.0 g) in water (260 ml) are combined in a flask. The temperature is set to 42° C. and the mixture is stirred until total dissolution of the solid. The aqueous phase is discharged and water (260 ml) is charged over the organic phase. The mixture is stirred for 15 minutes at 42° C. and then left to separate at 42° C. for 20 minutes. The aqueous phase is discharged and water (260 ml) is charged over the organic phase. This procedure is repeated twice. The resultant organic phase ("Solution of solifenacin base") is kept.

Acetone (260 ml), Succinic acid (12.7 g, 0.107 mol) and water (5 ml) are combined in a flask. The mixture is heated under reflux until total dissolution and then kept at 42° C. Then, the "Solution of solifenacin base" is charged and the mixture is heated to reflux and kept under reflux for 15 minutes. The content is distilled until a final volume of 260 ml. The mixture is cooled slowly until a final temperature of 3° C. and then filtered. The residue is washed with Ethyl acetate (50 ml) at 0/5° C. and is drained for 1 hour. The wet cake is dried in the vacuum oven at 60° C. to give a white solid.

Example 3

Synthesis of Solifenacin Succinate Amorphous Form 10 g of solifenacin succinate (example 2) were dissolved in 15 mL of water. The solution was frozen by nitrogen liquid and was placed in the freeze-drying equipment at −60° C. under vacuum. The sample was heated progressively in a period of time of 15 hours until at a final temperature of 25° C., 9 g of white solifenacin succinate amorphous form free of water were obtained. The amorphous form of solifenacin succinate was characterized by PXRD (FIG. 2). Three days later, the white solid had turned brown-colored and a sample analyzed by HPLC after ten days (method 2) showed a new impurity in an amount of 0.14% with a relative retention time of 0.93.

Example 4

Synthesis of Solifenacin Fumarate from Crude Solifenacin Base 120 ml of the "Solution of Solifenacin base in toluene" from example 1 (corresponding to about 8.9 g of solifenacine base) is distilled under vacuum. The crude solifenacin base obtained is dissolved in 50 ml of ethyl acetate. Meanwhile, 3.2 g of fumaric acid is dissolved in 64 ml of a mixture of acetone/water 98:2. This solution is added over the solifenacin base solution. The mixture is set to reflux for 15 minutes, and distilled until reaching a volume of 50 ml. Then, it is cooled slowly until a final temperature of 12° C., the resulting suspension is filtered and the solid is washed with ethyl acetate and dried in the vacuum oven at 60° C. to give 11.6 g of a white solid of Solifenacin Fumarate Crude. (HPLC-UV, method 1, RR (2.45%), SS (0.81%) and RS (ND)).

Example 5

Attempt to Synthesize Amorphous Solifenacin Fumarate Using Freeze-Drying 10 g of solifenacin fumarate (example 1) were dissolved in 600 ml of water at 60° C. The solution was frozen by nitrogen liquid and was placed in the freeze-drying equipment at −60° C. under vacuum. After 15 hours (following the method described in example 3), 10 g of white solifenacin fumarate (crystalline form) were obtained. The crystalline form of solifenacin fumarate was checked by PXRD and DSC analysis.

Example 6

Attempt to Synthesize Amorphous Solifenacin Fumarate Under Vacuum Drying 5 g of solifenacin fumarate (example 1) was dissolved in 50 ml of methanol (1% of water) and evaporated under vacuum at 50° C. In the flask a solid corresponding to the crystalline form of solifenacin fumarate is formed.

Example 7

Synthesis of Solifenacin Maleate (According to WO 2010/012459)

6 g of solifenacin base from example 1 was dissolved in 60 ml of isopropyl acetate; 1.92 g of maleic acid was added and the mixture was heated to 45° C. for 15 minutes. The mixture is kept at room temperature overnight. In these conditions a colorless oil is obtained.

Attempts with the other solvents or mixtures of solvents were done in order to obtain solifenacin maleate in crystalline form. All of them were unsuccessful. Examples of the procedures used in order to attempt obtaining a crystalline form are:

4 g of solifenacin base is dissolved in 20 ml of ethyl acetate; 1.28 g of maleic acid dissolved in 20 ml of ethyl acetate is added and the mixture is heated to reflux for 15 minutes. The mixture is distillated and cooled at 0° C. In these conditions colorless oil is obtained.

4 g of solifenacin base is dissolved in 20 ml of isopropyl acetate; 1.28 g of maleic acid dissolved in 20 ml of isopropyl acetate is added and the mixture is heated to reflux for 15 minutes, 2 ml of methanol are added. The mixture is distillated and cooled at 0° C. In these conditions colorless oil is obtained.

4 g of solifenacin base is dissolved in 20 ml of isopropyl alcohol; 1.28 g of maleic acid dissolved in 20 ml of acetonitrile is added and the mixture is heated to reflux for 30 minutes. The mixture is distillated and cooled at room temperature. In these conditions colorless oil is obtained.

3.5 g of solifenacin base is dissolved in 35 ml of isopropyl alcohol; 1.1 g of maleic acid is added and the mixture is heated to reflux for 30 minutes. The mixture is distillated and cooled at 0° C. In these conditions colorless oil is obtained.

The experience of the present inventors is therefore that obtaining a crystalline form of solifenacin maleate is considerably more complicated than obtaining a fumarate salt according to the present invention. In addition, based on WO 2010/012459, the maleate salt seems to have a much higher tendency towards forming the amorphous form.

Example 8

Preparation of Tablets of Solifenacin Salts 25 parts by weight of Hypromellose (Pharmacoat 603) are dissolved and agitated in 130 parts of purified water with an air motor stirrer (IMA) to prepare a binder solution (at a concentration of 20.0% (w/v)). Then, 50 parts of solifenacin salt, 389 parts of lactose monohydrate (Granulac) and 128 parts of corn starch (C*PharmGel 03406) are mixed together (pre-mix) in a single pot granulator (IMA Zanchetta 3 L capacity).

The binder solution is sprayed over the pre-mix at room temperature with a flow rate of 60 ml/min, impeller speed of 300 rpm and chopper speed of 1500 rpm for wet granulation. After spraying, kneading takes place for 3 min with impeller speed of 300 rpm. After granulation, the granules are dried at a charged temperature of the jacket bowl of 80° C. under vacuum conditions, tilting movement of the bowl of 90° and intermittent speed (120 rpm) of the impeller for 120 seconds.

The granules are dried until a final moisture of 2.5%-1.0% has been reached. 6 parts of magnesium stearate are added to the dried granules for blending with a biconic mixer (SAR Labortecnic). Thereafter, the resulting mixture is compressed with a rotary tabletting machine (KILIAN IMA Pressima) with 6.0 mm punches at a compression pressure sufficient to achieve a hardness of the tablet of more than 50 N and a tablet weight of 60 mg.

The resulting tablets are coated in a non perforated pan (IMA, type HT25). Coating is performed with a solution prepared by dissolving 20 parts of Opadry II pink (Colorcon) in 200 parts of purified water using an air motor stirrer (IMA). Coating is achieved at a charge air temperature of 60-80° C., a pan rotation velocity of 6-13 rpm, and coating fluid feed rate of 16-40 ml/min for a 3.3% ratio of the component to the tablet weight, to obtain the film-coated tablet.

Example 9

Stability of Tablets of Solifenacin Salts

The stability of tablets formulated with solifenacin succinate and solifenacin fumarate, respectively, was tested in a side-by-side comparison. For both salts the crystalline form was used for formulating the tablets, using the preparation method according to Example 8. For both salts the amount of solifenacin was assayed by HPLC at 0, 3 and 6 months and the amount of "F1 impurity" was also measured. The results are provided in the tables below and are illustrated in FIGS. 9 and 10.

| | SOLIFENACIN SUCCINATE | | |
|---|---|---|---|
| TEST | INITIAL | 3 MONTHS | 6 MONTHS |
| DESCRIPTION | pink biconvex cylindrical tablet | pink biconvex cylindrical tablet | pink biconvex cylindrical tablet |
| HARDNESS | 98N | 98N | 102N |
| LOSS ON DRYING | 2.40% | 2.43% | 2.39% |
| MEDIUM WEIGHT | 125.57 mg | 124.80 mg | 126.26 mg |
| ASSAY AMOUNT | 98.7% | 96.8% | 94.7% |
| CHROMATOGRAPHIC IMPURITY | <0.05% | <0.06% | 0.91% |

| | SOLIFENACIN FUMARATE | | |
|---|---|---|---|
| TEST | INITIAL | 3 MONTHS | 6 MONTHS |
| DESCRIPTION | pink biconvex cylindrical tablet | pink biconvex cylindrical tablet | pink biconvex cylindrical tablet |
| HARDNESS | 75N | 73N | 66N |
| LOSS ON DRYING | 2.05% | 2.01% | 2.24% |
| MEDIUM WEIGHT | 124.54 mg | 124.21 mg | 125.51 mg |
| ASSAY AMOUNT | 98.2% | 99.4% | 99.6% |
| CHROMATOGRAPHIC IMPURITY | <0.05% | <0.05% | <0.05% |

| | PLACEBO | | |
|---|---|---|---|
| TEST | INITIAL | 3 MONTHS | 6 MONTHS |
| DESCRIPTION | pink biconvex cylindrical tablet | pink biconvex cylindrical tablet | pink biconvex cylindrical tablet |
| HARDNESS | 74N | 77N | 71N |
| LOSS ON DRYING | 2.44% | 2.54% | 2.51% |
| MEDIUM WEIGHT | 125.26 mg | 124.64 mg | 126.00 mg |
| ASSAY AMOUNT | N/A | N/A | N/A |
| CHROMATOGRAPHIC IMPURITY | n.d. | n.d. | n.d. |

The results clearly demonstrate that the fumarate salt is much more stable than the succinate salt and that the succinate salt starts degrading right away. The results furthermore show that the amount of "F1" impurity increases in the 6 month period for the succinate salt, whereas it remains at the constant low level for the fumarate salt.

The invention claimed is:

1. A fumarate salt of solifenacin.

2. The fumarate salt according to claim 1, wherein said fumarate salt is a hydrogenfumarate (1:1) salt.

3. The fumarate salt according to claim 1, wherein said fumarate salt is substantially crystalline.

4. A pharmaceutical composition comprising the fumarate salt according to claim 1 and one or more pharmaceutically acceptable carriers, wherein said pharmaceutical composition is a solid formulation.

5. The pharmaceutical composition according to claim 4, wherein said pharmaceutical composition is formulated for oral administration.

6. The pharmaceutical composition according to claim 4, wherein said pharmaceutical composition is in the form of a tablet, a capsule, a gelcap, a granule, a sachet or a pill.

7. The pharmaceutical composition according to claim 6, wherein said pharmaceutical composition is in the form of a tablet.

8. A process for preparing solifenacin or a pharmaceutically acceptable salt thereof comprising:
 a) reacting a solifenacin base with a fumaric acid to form a fumarate salt thereof; and
 b) optionally transforming the fumarate salt obtained in step a) to solifenacin base and/or a different pharmaceutically acceptable salt of solifenacin.

9. The process according to claim 8, wherein step a) is preceded by the steps:
 a') reacting 1(S)-1-phenyl-1,2,3,4-tetrahydroisoquinoline with a C1-6 alkyl chloroformate to form a corresponding carbamate;
 b') reacting the carbamate resulting from step a') with 3R-quinuclidinol in the presence of a strong base so as to form a solifenacin base; and
 c') optionally, isolating the solifenacin base;
 wherein the solifenacin base used in step a) is the base obtained in step b') or step c').

10. The process according to claim 9, wherein a mixture of non-polar solvent and polar solvent is used in step b').

11. The process according to claim 10, wherein the polar solvent is present in an amount of 1 to 20% (v/v) of the combined solvent volume.

12. The process according to claim 9, wherein the excess 3R-quinuclidinol resulting from step b') is recovered by cooling the mixture to a temperature not exceeding 15° C., stirring the mixture for at least 20 minutes at said temperature, and collecting the formed precipitate.

13. The process according to claim 12, wherein water is added upon cooling of the mixture in an amount of up to 20% (v/v) of the non-polar solvent.

14. The process according to claim 8, wherein said fumarate salt is further purified by suspending the fumarate salt in a mixture of polar solvents, and stirring for a time period sufficient to obtain (S,S)-solifenacin fumarate with an optical purity so that the amount of each of the (R,R)-, (R,S)-, and (S,R)-enantiomers is 0.2% or less of the total amount of solifenacin fumarate.

15. A method of treating an overactive bladder in a patient comprising providing a fumarate salt of solifenacin to a patient that has an overactive bladder.

16. The method of claim 15, wherein said fumarate salt of solifenacin is formulated for oral administration.

17. The method according to claim 16, wherein said formulation for oral administration is a tablet, a capsule, a gelcap, a granule, a sachet or a pill.

\* \* \* \* \*